US008367642B2

(12) United States Patent
Brown et al.

(10) Patent No.: US 8,367,642 B2
(45) Date of Patent: *Feb. 5, 2013

(54) METHODS OF PREVENTING OR TREATING DISEASES AND CONDITIONS USING COMPLEX CARBOHYDRATES

(75) Inventors: Harold G. Brown, Parksville, MO (US); Karen K. Brown, Parksville, MO (US); Carol A. Cooper, Pittsburgh, PA (US)

(73) Assignee: Dermal Research Laboratories, Inc., Parksville, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/006,975

(22) Filed: Jan. 14, 2011

(65) Prior Publication Data

US 2011/0112049 A1    May 12, 2011

Related U.S. Application Data

(62) Division of application No. 10/343,240, filed as application No. PCT/US01/41473 on Jul. 31, 2001, now Pat. No. 7,879,824.

(60) Provisional application No. 60/222,046, filed on Jul. 31, 2000.

(51) Int. Cl.
    *A61K 31/70* (2006.01)
(52) U.S. Cl. .......................................... 514/62
(58) Field of Classification Search .............. 514/62
    See application file for complete search history.

(56) References Cited

U.S. PATENT DOCUMENTS

| | | |
|---|---|---|
| 3,895,107 A | 7/1975 | Morrison |
| 4,141,973 A | 2/1979 | Balazs |
| 4,148,893 A | 4/1979 | Smith |
| 4,248,861 A | 2/1981 | Schutt |
| 4,303,676 A | 12/1981 | Balazs |
| 4,353,896 A | 10/1982 | Levy |
| 4,440,777 A | 4/1984 | Zupan |
| 4,463,016 A | 7/1984 | Burgess |
| 4,474,763 A | 10/1984 | Lubowe |
| 4,521,411 A | 6/1985 | Koloff |
| 4,564,521 A | 1/1986 | Altadonna |
| 4,585,656 A | 4/1986 | Rosenthal et al. |
| 4,707,354 A | 11/1987 | Garlen et al. |
| 4,708,873 A | 11/1987 | Schulte |
| 4,736,024 A | 4/1988 | Della Valle et al. |
| 4,782,046 A | 11/1988 | Brown et al. |
| 4,797,402 A | 1/1989 | Dorsey |
| 4,800,197 A | 1/1989 | Kowcz et al. |
| 4,808,576 A | 2/1989 | Schultz |
| 4,847,078 A | 7/1989 | Sheppard et al. |
| 4,883,664 A | 11/1989 | Sharkey |
| 4,895,727 A | 1/1990 | Allen |
| 4,900,550 A | 2/1990 | Lowry |
| 4,917,890 A | 4/1990 | McNalley |
| 4,933,183 A | 6/1990 | Sharma et al. |
| 4,933,184 A | 6/1990 | Tsuk |
| 4,973,473 A | 11/1990 | Schneider et al. |
| 5,009,890 A | 4/1991 | Dipippo |
| 5,013,726 A | 5/1991 | Ivy et al. |
| 5,028,429 A | 7/1991 | Gochenouer |
| 5,073,366 A | 12/1991 | Beck |
| 5,079,260 A | 1/1992 | Weitzberg et al. |
| 5,082,656 A | 1/1992 | Hui et al. |
| 5,096,709 A | 3/1992 | Vandersloot |
| 5,106,622 A | 4/1992 | Sherwood et al. |
| 5,166,331 A | 11/1992 | Della Valle et al. |
| 5,179,086 A | 1/1993 | Flender |
| 5,215,759 A | 6/1993 | Mausner |
| 5,223,257 A | 6/1993 | Arora |
| 5,266,318 A | 11/1993 | Taylor-McCord |
| 5,308,838 A | 5/1994 | McAnalley et al. |
| 5,331,012 A | 7/1994 | Riddick et al. |
| 5,350,774 A | 9/1994 | Palou |
| 5,362,497 A | 11/1994 | Yamada et al. |
| 5,460,821 A | 10/1995 | Masiz |
| 5,559,103 A | 9/1996 | Gaeta et al. |
| 5,604,200 A | 2/1997 | Taylor-McCord |
| 5,773,425 A | 6/1998 | McAnalley et al. |
| 5,888,984 A | 3/1999 | Brown |
| 5,929,050 A | 7/1999 | Petito |
| 5,965,152 A | 10/1999 | Galin et al. |
| 6,083,933 A | 7/2000 | Hahn |
| 6,391,864 B1 | 5/2002 | Stone |
| 6,432,929 B1 | 8/2002 | Stone |
| 6,875,753 B1 * | 4/2005 | Pilarski .................... 514/54 |
| 6,924,273 B2 | 8/2005 | Pierce |
| 2002/0068718 A1 | 6/2002 | Pierce |

FOREIGN PATENT DOCUMENTS

| | | |
|---|---|---|
| CA | 2 156 013 A1 | 2/1997 |
| DE | 19520575 A1 | 12/1996 |
| DE | 195 47 105 A1 | 6/1997 |
| EP | 0 130 550 A2 | 1/1985 |
| EP | 0 254 845 A2 | 2/1988 |
| EP | 0 444 492 B1 | 9/1991 |
| EP | 0 497 162 A1 | 8/1992 |

(Continued)

OTHER PUBLICATIONS

Adams et al., The Lancet, vol. 343, pp. 831-836 (Apr. 1994).

(Continued)

*Primary Examiner* — Zohreh Fay
(74) *Attorney, Agent, or Firm* — Birch, Stewart, Kolasch & Birch, LLP

(57) ABSTRACT

The invention relates to a method of preventing and treating diseases and conditions associated with allergies, autoimmunity, the adhesion cascade, the metastatic cascade or the coronary cascade comprising administering (i) at least one complex carbohydrate as the sole active ingredient, or (ii) at least one pharmaceutical composition which comprises as an active ingredient a pharmacologically effective amount of at least one low purity or cosmetic grade complex carbohydrate selected from the group consisting of oligosaccharides, sialylated oligosaccharides, polysaccharides and glycosaminoglycans, and an effective amount of at least one transdermal or transmucosal carrier in an amount effective to deliver the complex carbohydrate into the blood stream.

3 Claims, 2 Drawing Sheets

FOREIGN PATENT DOCUMENTS

| | | |
|---|---|---|
| EP | 0 509 120 A1 | 10/1992 |
| EP | 0 704 216 A1 | 4/1996 |
| EP | 0 795 560 A1 | 9/1997 |
| EP | 0 852 236 A1 | 7/1998 |
| FR | 26 74749 A1 | 10/1992 |
| JP | 59-163307 A | 9/1984 |
| JP | 62-77308 S | 4/1987 |
| JP | 63-008309 A1 | 1/1988 |
| JP | 01 186824 A1 | 7/1989 |
| JP | 04 041431 A | 2/1992 |
| JP | 5-66149 A | 3/1993 |
| JP | 06 107550 A | 4/1994 |
| JP | 9-262057 A | 10/1997 |
| WO | WO 87/05517 A1 | 9/1987 |
| WO | WO 88/01280 A1 | 2/1988 |
| WO | WO 90/00058 A1 | 1/1990 |
| WO | WO 91/13624 A1 | 9/1991 |
| WO | WO 92 11780 A1 | 7/1992 |
| WO | WO 92/18546 A1 | 10/1992 |
| WO | WO 92/22585 A1 | 12/1992 |
| WO | WO 93/05075 A1 | 3/1993 |
| WO | WO 93/09766 A1 | 5/1993 |
| WO | WO 95/23805 A1 | 9/1995 |
| WO | WO 95 31177 A1 | 11/1995 |
| WO | WO 95/34286 A1 | 12/1995 |
| WO | WO 96/05845 A3 | 2/1996 |
| WO | WO 96/06622 A1 | 3/1996 |
| WO | WO 96/32492 A1 | 10/1996 |
| WO | WO 97/25051 A1 | 7/1997 |
| WO | WO 97/33592 A1 | 9/1997 |
| WO | WO 97/40841 A1 | 11/1997 |
| WO | WO 97/45435 A1 | 12/1997 |
| WO | WO 98/06730 A1 | 2/1998 |
| WO | WO 98/08854 A2 | 3/1998 |
| WO | WO 00/08061 A1 | 2/2000 |

OTHER PUBLICATIONS

Article: Essense Oils, 2 pages.
Chemistry 470—"Industrial Chemistry", Spring 2004, Internet, 6 pages.
Claire Parisel et al., Interactions of heparin with human skin cells: Binding, location, and transdermal penetration (article), Accepted Mar. 4, 2003, pp. 517-523. 2003, Wiley Periodicals. Inc.
Collins & Ferrier, Monosaccharides: Their Chemistry and Their Roles in Natural Product, (John Wiley & Sons), p. 4, (1995).
Corbett, Spec. Chem., vol. 11(7), pp. 493-496, pp. 501-502 (1991) (Abstract Only).
D. Kobayashi et al., Pharmaceutical Research, vol. 11, No. 1, 1994, Analysis of the Combined Effect of 1-Menthol and Ethanol as Skin Permeation Enhancers Based on a Two-Layer Skin Model (article), accepted Jun. 22, 1993, pp. 96-103.
David C. Steinberg, Cosmetic Technology, Mucopolysaccharides for Cosmetics, (Feb. 1982), pp. 41-44.
David C. Steinberg, Report, 25 pages.
Dr. Karen K. Brown, Notes: D000459 and D000460: Jan. 9, 1992 and Jan. 18, 2002, 2 pages.
Dsaqupta & Tang, Modern Synthetic Carbohydrate Chemistry, (ACS-Short Course, Aug. 19-20, 1994, Washington D.C.).
Ed. Sybil Parker, McGraw-Hill Dictionary of Chemical Terms (McGraw-Hill, Inc.), p. 278 (1984).
Elkhouly et al.: Australian Journal of Pharmaceutical Sciences, vol. 9, pp. 81-84 (Sep. 1980).
Foxhall et al, The Journal of Cell Biology, vol. 117(4), pp. 895-902 (1992).
Gregor Cevc et al., Biochimica et Biophysica Acta, vol. 1368, (1998), Ultraflexible vesicles, Transfersomes, have an extremely low pore penetration resistance and transport therapeutic amounts of insulin across the intact mammalism skin, pp. 201-215.
Gregory M. Glenn et al., Cutting Edge: Transcutaneous Immunization with Cholera Toxin Protects Mice Against Lethal Mucosal Toxin Challenge (article), pp. 3211-3214.
Gregory M. Glenn et al., Nature, vol. 391, Skin immunization made possible by cholera toxin (article), (Feb. 26, 1998), 1 page.
Hans Schaefer et al.; Skin Barrier (article), 3 pages, Karger.

Howard et al., The Compendium, vol. 15, No. 3, pp. 473-479 (Mar. 1993).
Ibrahim, Pharm. Acta Helv., vol. 66, pp. 286-288 (1991).
Lasky, Annual Review of Biochemistry, vol. 64, pp. 1B-139B (1995).
Lawrence et al., Progress in Essential Oils, Perfumes & Flavorist, vol. 17, pp. 51-60 (Sep. 1980).
Marc Cohen et al., The Journal of Rheumatology, vol. 30, No. 3, (2003) A Randomized Double Bind, Placebo Controlled Trial of a Topical Cream Containing Glucosamine Sulfate, Chondroitin Sulfate, and Camphor for Osteoarthritis of the Knee, pp. 523-528.
Marie Curie and the Science of Radioactivity—Research Breakthroughs (1897-1904), 2 pages, 2000-2004 American Institute of Physics.
Munro et al., American Journal of Pathology, vol. 141, No. 6, pp. 1397-1408 (Dec. 1992).
*Naturopathic Laboratories International, Inc.*, Plaintiff v. *Dermal Research Laboratories, Inc.*, Defendant, Deposition of Karen Brown. PhD.; Oct. 23, 2003; 335 pages; U.S. District Court for the Western District of Missouri Western Division.
*Naturopathic Laboratories International, Inc.*, Plaintiff, v. *Dermal Research Laboratories, Inc.*, Defendant, Claim Construction of '984 Patent: Jan. 23, 2004; 11 pages; U.S. District Court for the Western Division.
*Naturopathic Laboratories International, Inc.*, Plaintiff, v. *Dermal Research Laboratories, Inc.*, Defendant, Complaint, 8 pages, U.S. District Court for the Western District of Missouri Western Division.
*Naturopathic Laboratories International, Inc.*, Plaintiff, v. *Dermal Research Laboratories, Inc.*, Defendant, Deposition of Carol Cooper, Ph.D.; Feb. 17, 2004; 339 pages; U.S. District Court for the Western District of Missouri Western Division.
*Naturopathic Laboratories International, Inc.*, Plaintiff, v. *Dermal Research Laboratories, Inc.*, Defendant, Deposition of Harold Brown, Ph.D. Feb. 26, 2004; 335 pages; U.S. District Court for the Western District of Missouri Western Division.
*Naturopathic Laboratories International, Inc.*, Plaintiff, v. *Dermal Research Laboratories, Inc.*, Defendant, Dermal Research Laboratories, Inc.'s Answer and Counterclaim to Naturopathic Laboratories International Inc.'s Complaint, 14 pages, U.S. District Court for the Western District of Missouri Western Division.
*Naturopathic Laboratories International, Inc.*, Plaintiff, v. *Dermal Research Laboratories, Inc.*, Defendant, Expert Rebuttal to the Invalidity Report of Mar. 8, 2004, Regarding United States Patent No. 5,888,984, Apr. 9, 2004, 27 pages.
*Naturopathic Laboratories International, Inc.*, Plaintiff, v. *Dermal Research Laboratories, Inc.*, Defendant, Plaintiff Naturopathic Laboratories, International, Inc.'s Response to Defendant's First set of Interrogatories, 14 pages, U.S. District Court for the Western District of Missouri Western Division.
*Naturopathic Laboratories International, Inc.*, Plaintiff, v. *Dermal Research Laboratories, Inc.*, Defendant, Reply of Naturopathic Laboratories International, Inc., to Counterclaim of Dermal Research Laboratories, Inc., 6 pages, U.S. District Court for the Western District of Missouri Western Division.
*Naturopathic Laboratories International, Inc.*, Plaintiff, v. *Dermal Research Laboratories, Inc.*, Defendant, Suggesions in Support of Dermal Research Laboratories, Inc.'s Motion for Summary Judgment on Naturopathic Laboratories International, Inc.'s Invalidity Defenses; Jun. 7, 2004; 27 pages; U.S. District Court for the Western District of Missouri Western Division.
Nelson et al., Blood, vol. 82 (11), pp. 3253-3258 (1993) (Abstract Only).
Non-Final Office Action dated Feb. 12, 2004 in U.S. Appl. No. 09/890,425.
Non-Final Office Action dated Jan. 25, 2008 in U.S. Appl. No. 09/890,425.
Non-Final Office Action dated Jul. 12, 2005 in U.S. Appl. No. 09/890,425.
Non-Final Office Action dated Mar. 15, 2007 in U.S. Appl. No. 09/890,425.
Non-Final Office Action dated Oct. 6, 2009 in U.S. Appl. No. 09/890,425.
Office Action issued in corresponding Canadian Patent Application No. 2,417,867 issued on Apr. 16, 2010.

Pankaj Karande et al., Nature Biotechnology—Advance Online Publication, Discovery of transdermal penetration enhancers by high-throughput screening (article), published online (Jan. 4, 2004), pp. 1-6.

Radin et al., The Journal of Bone and Joint Surgery, vol. 54-A, pp. 607-616 (Apr. 1972).

Raghavachari et al., Journal of Pharmaceutical Sciences, vol. 91, No. 3, (Mar. 2002), Targeted Gene Delivery Vehicles, 9 pages.

Santus et al., J. Controlled Release, vol. 25, pp. 1-20 (1993).

Shimizu et al., Journal of Immunology, vol. 143, pp. 2457-2463, (Oct. 1989).

Srivas R. Srinivas, Atlas of Essential Oils, 2 pages.

Tanya Scharton-Kersten et al., Infection and Immunity, vol. 68, No. 9, Transcutaneous Immunization with Bacterial ADP-Ribosylating Exotoxins, Subunits, and Unrelated Adjuvants (Sep. 2000), pp. 5306-5313.

The 1998 CIR Expert PANEM Members; Chairman Wilma Bergfeld, MD, FACP. Donald Belsito, MD, Wlliam Cariton, PhD., DVM., Curtis Klaassen, PhD., Arnold L. Schroeter, MD, and Ronald C. Shank, PhD., and Thomas Saga, PhD, CIR Director; F Alan Andersen, PhD, Final Report: Safety Assessment of Peppermint, Sep. 11, 1998, 18 pages, Cosmetic.

The Merck Index, 11th Edition, pp. 735, pp. 1072-1078 (1989).

Tyrrell et al., Proc. Natl. Acad. Sci. USA, vol. 88, pp. 10372-10376 (Nov. 1991).

Williams et al., International Journal of Pharmaceutics, vol. 57, R7-R9 (1989).

Yagi et al., Journal of Pharmaceutical Sciences, vol. 73, pp. 62-65, No. 1 (Jan. 1984).

* cited by examiner

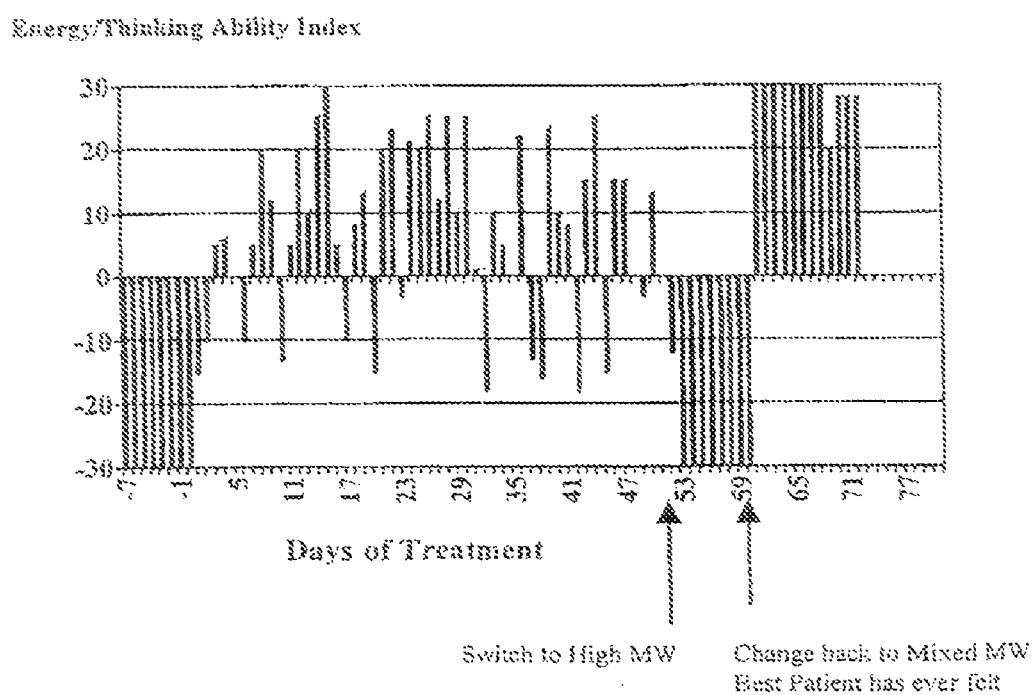
Figure 1   Response of ADD Patient to Oral Treatment with Sodium Hyaluronate

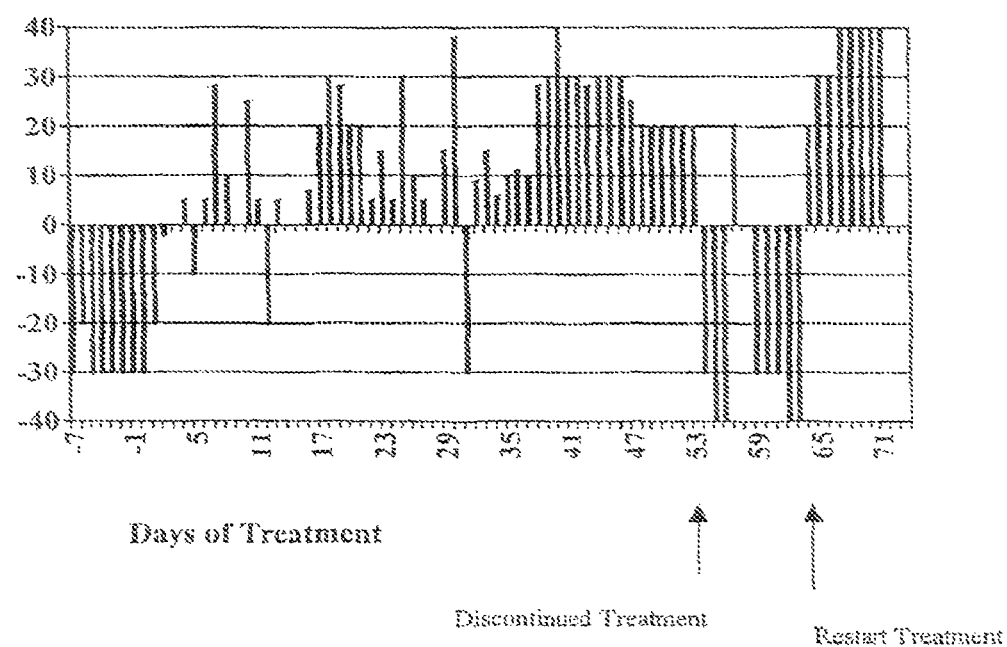
Figure 2   Response of ADHD Patient to Oral Treatment with Sodium Hyaluronate

METHODS OF PREVENTING OR TREATING DISEASES AND CONDITIONS USING COMPLEX CARBOHYDRATES

CROSS-REFERENCE TO RELATED APPLICATION

This application is a Divisional Application of application Ser. No. 10/343,240 filed on May 16, 2003 now U.S. Pat.No. 7,879,824, and application Ser. No. 10/343,240 is the national phase of PCT International Application No. PCT/US01/41473 filed on Jul. 31, 2001 under 35 U.S.C. §371, and PCT International Application No. PCT/US01/41473 claims priority under 35 U.S.C. 119 of Provisional Application 60/222,046 filed Jul. 31, 2000. The entire contents of each is herein incorporated by reference.

FIELD OF THE INVENTION

The invention relates to novel uses for a composition of matter comprising complex carbohydrates preferably as the sole active ingredient, applied topically, orally, mucosally or parenterally to prevent or treat diseases and conditions associated with allergies or the adhesion, metastatic or coronary cascades. Also disclosed are methods of preventing and treating the above-mentioned diseases and conditions by administering the complex carbohydrates of the present invention. Additionally, this invention describes novel uses for a composition of matter comprising at least one complex carbohydrate and at least one transdermal or transmucosal carrier useful for effecting transdermal or transmucosal migration resulting in topical or mucosal delivery of macromolecules, through the skin or mucous membranes of mammals and into the bloodstream. Methods of preventing diseases and conditions of mammals associated with allergies, autoimmune mechanisms, the adhesion cascade, the metastatic cascade and the coronary cascade are also described wherein the combination of complex carbohydrates with essential oils is applied topically, orally, mucosally or parenterally on a repeated basis until treatment is complete.

BACKGROUND OF THE INVENTION

For purposes of this invention, complex carbohydrates are defined as any polymer comprising more than two sugar moieties and include such classes of compounds as polysaccharides and oligosaccharides. Polysaccharides include mucopolysaccharides and mannans whereas oligosaccharides are comprised of branched polysaccharides such as sialylated sugars including milk sugars. The key milk sugars (also called hexaoses) incorporated in the general class of complex carbohydrates are difucosyllacto-N-hexaose a and b, Disialyl-monofucosyllacto-N-hexaose and monofucosyl-lacto-N-hexsaose I, II, and II (obtainable from Oxford Glycosystems, Inc.).

One of the most active areas of research at present is the study of the genetics and function of mucopolysaccharides. These are glycosaminoglycans that can be obtained from numerous sources {e.g. rooster combs, trachea, umbilical cords, skin, articular fluids and certain bacteria such as Streptococci spp). Most glycosaminoglycans (hyaluronic acid, chondroitin sulfates A, B, and C, heparin sulfate, heparin, keratan sulfate, dermatan sulfate, etc.) are composed of repeating sugars such as n-acetylglucosamine, glucuronic acid and n-acetyl galactosamine (these are known as non-sulfated glycosaminoglycans). If such glycosaminoglycans contain sulfur groups they are known as sulfated glycosaminoglycans.

Heparin, hyaluronic acid and chondroitin sulfate are the most studied mucopolysaccharides. Heparin has been used for a number of years as an anticoagulant. Hyaluronic acid has been used therapeutically since the 1970s as a replacement for the vitreous humor of the eye post surgery and, more recently, as replacement for joint fluid in arthritic joints. The mode of action for hyaluronic acid injected directly into joints for treatment of arthritis has been proposed to be lubrication and replacement of the degraded joint fluid with highly viscous hyaluronic acid. High molecular weight (>750,000 daltons) and high viscosity have been reported to be critical for this use. (For purposes of this patent, all molecular weights are expressed as daltons. The unit designation will not be added hereinafter.)

In the 1980s, it was discovered that chondroitin sulfate, or polysulfated glycosaminoglycan (known by its commercial name as ADEQUAN®) could be injected intramuscularly for reduction of pain and inflammation associated with arthrosis of horses. The mechanism of action of this glycosaminoglycan has been speculated to be inhibition of certain degradative enzymes present in the joint fluid that are up-regulated by trauma.

In the 1990s, chondroitin sulfate had developed into a popular nutritional supplement being used extensively to treat joint problems. Such treatment requires oral doses between 1000 and 3000 mg/day for humans. Even with these high doses (>15 mg/Kg), relief from joint pain often takes 6-9 months.

In 1989, it was discovered that intravenous, intramuscular or subcutaneous delivery of hyaluronic acid could reduce the pain of arthritis (U.S. Pat. No. 4,808,576 by Schultz et al) when the hyaluronic acid was delivered remote to the site of the arthritis (not into the joint). This Schultz et. al. patent specifically states that the hyaluronic acid must be of high purity (>99% pure hyaluronic acid). No mention is made of use of other complex carbohydrates, mucopolysaccharides or glycosaminoglycans administered by any method, or use of hyaluronate sodium orally or mucosally, use of low purity glycosaminoglycans or treatment of other diseases or conditions by parenteral administration.

The importance of high molecular weight for effectiveness of hyaluronic acid in the treatment of arthritis is generally emphasized (see for example Balazs, U.S. Pat. No. 4,141,973 and Howard and McIlraith, The Compendium, 15(3), March 1993) who summarize several clinical studies conducted to determine the most efficacious molecular weight range of hyaluronic acid injected intra-articularly to treat traumatic arthritis in horses. The conclusion from these studies was that hyaluronic acid with a molecular weight below $1 \times 10^6$ was not as effective as hyaluronic acid with a molecular weight above this value.

The most recent studies on hyaluronic acid discuss treatment of various types of cancer with very large doses of this macromolecule (Falk, WO 97/40841). This Falk application suggests that doses should exceed 750 mg per 70 Kg person, preferably, exceeding 1 g per 70 Kg person. This dose level calculates to be approximately 10-20 mg/Kg. Such doses are given intermittently post diagnosis and are not suggested to be preventative or administered in continuous low doses. Additionally, it is clear that the sodium hyaluronate of the Falk invention needs to be pure enough for injection even though oral administration is used in addition to intravenous injection. In all cases, patients were treated with hyaluronan in addition to chemotherapy. Hyaluronan was not used as the sole active ingredient for treatment of the cancer patients by Falk.

The adhesion cascade was first described in the early 1990s. In a summary by Adams and Shaw (The Lancet, 343, Apr. 2, 1994) the adhesion cascade is supposed to describe the mechanism by which pain and swelling are produced post trauma. It is divided into four sequential steps of tethering, triggering, strong adhesion and motility. Tethering interactions are mediated by a family of three lectin-like carbohydrate-binding molecules (selectins). These interactions are strong enough to cause the leukocytes to roll along the blood vessel walls to the site of trauma instead of flowing freely through such vessels as they would in a non-traumatized state. The triggering response is stimulated by factors such as cytokines stimulated by a traumatic event and mediated by adhesion molecules called integrins. Integrins, by themselves, do not bind well to epithelium. However, when activated, integrins promote strong adhesion of the leukocyte to the epithelial surface. Leukocytes bind to the epithelial cells via their receptor sites such as CD44, CD31, etc. By a mechanism of attachment and detachment the leukocytes are guided to the site of trauma. At the site of trauma the adhesion to the blood vessel wall becomes stronger and the interaction of these integrins with their ligands on the surface of the leukocytes are responsible for cessation of movement and flattening of the leukocyte. Finally, a process involving VCAM-1 and LFA-1 and other such integrins allows leukocytes to pass between endothelial cell junctions and into the tissue that has been traumatized. Collection of leukocytes at the site of trauma produces inflammation which is then followed by pain or other sequelae.

The metastatic cascade is very similar to the adhesion cascade. It has been proposed that tumor cells of all types contain CD44 receptor sites on their surface. These CD44 receptor sites appear to be involved in metastasis functioning similar to the receptor sites on leukocytes □ tethering the tumor cells to the blood vessel wall and providing the motility necessary for movement from one site to another in the mammalian body. A significant portion of the literature on CD44 and tumor cells/cancer teaches that hyaluronic acid or hyaluronan actually stimulates metastasis (Eur. J. Cancer, 1999, March; 35 (3), 473-480).

A coronary cascade has recently been described in the Harvard Health Letter (December 1999, pg. 4-5) and SCIENCE vol: 285, 23 Jul., 1999, pg 595-599). This cascade describes a new mechanism to explain the development of heart disease and stroke. Rather than the traditional theory that plaques are formed by a collection of cholesterol alone, the new theory is based on the premise that there are stable and unstable plaques produced on blood vessel walls. Unstable plaques are the problem plaques because they are "swarming with T cells and macrophages" that are responding to a site of trauma and triggering the adhesion cascade resulting in inflammation. It is the "swarming T cells and macrophages" that make these plaques unstable. The T cells are described as sending macrophages a signal to release a protein called tissue factor which "spills out and encounters circulating blood, attracting platelets and triggering formation of a clot that quickly blocks up the artery".

Accordingly, it is totally unexpected that complex carbohydrates of the present invention could be administered topically, orally, mucosally or parenterally, in low doses, to prevent and treat diseases and conditions associated with allergies, the adhesion cascade, the metastatic cascade and the coronary cascade described herein.

BRIEF DESCRIPTION OF THE DRAWINGS

FIG. 1 is a graph demonstrating the effect of treating an adult suffering with Attention Deficit Disorder with various formulations of hyaluronic acid.

FIG. 2 is a graph demonstrating the effect of treating a 9 year old child suffering from Attention Deficit Hyperactivity Disorder with hyaluronic acid.

SUMMARY OF THE INVENTION

The present invention relates to a method of preventing and treating diseases and conditions associated with allergies, autoimmunity, the adhesion cascade, the metastatic cascade or the coronary cascade comprising administering (i) at least one complex carbohydrate as the sole active ingredient, or (ii) at least one pharmaceutical composition which comprises as an active ingredient a pharmacologically effective amount of at least one low purity or cosmetic grade complex carbohydrate selected from the group consisting of oligosaccharides, sialylated oligosaccharides, polysaccharides and glycosaminoglycans, and an effective amount of at least one transdermal or transmucosal carrier (e.g. essential oil) in an amount effective to deliver the complex carbohydrate into the blood stream.

Accordingly, the present invention relates to using complex carbohydrates, including but not limited to mucopolysaccharides and glycosaminoglycans, to bind to the receptor sites on leukocytes (e.g. CD44 and CD31) blocking their ability to tether to the blood vessel walls, inhibiting the motility to the site of trauma thus reducing the pain, swelling and other sequelae associated therewith (interrupting the adhesion cascade). Additionally, the present invention teaches that complex carbohydrate molecules, including but not limited to mucopolysaccharides and glycosaminoglycans, bind to the receptor sites on tumor cells blocking their ability to tether to the blood vessel walls and inhibit the tumor motility which, in turn, inhibits the potential for metastasis.

The compositions of the present invention inhibit the macrophages from swarming to a site of irritation or trauma on a blood vessel wall wherein said macrophages would normally accumulate producing the unstable plaques described previously, thus preventing and treating heart disease and stroke. Additionally, the compositions of the present invention inhibit the T-cell and macrophage "swarming" thus blocking the release of the tissue factor (referred to previously) and preventing cardiac events caused by said ruptured plaques.

In another embodiment of the present invention allergies and allergy-related diseases, diseases associated with the bodies' adverse reactions to stimuli such as foods, inhalants and drugs wherein said adverse reactions include but not limited to Attention Deficit Disease, Attention Deficit Hyperactivity Disease, interstitial cystitis, autism, migraines, asthma, Turret's Syndrome, fibromyalgia, anaphylaxis, rhinitis, sinusitis and inflammation providing the environment for yeast infections, bacterial infections or virus infections and autoimmune diseases wherein the bodies' macrophages attack its own body tissues and organs producing diseases including but not limited to rheumatoid and osteoarthritis, Lupus Erythematosis, multiple sclerosis, polymyositis, muscular dystrophy, Diabetes, and potentially Alzheimer's Disease, are associated by a mechanism similar to the adhesion cascade. Therefore, CD44, CD31, RHAMM and other similar receptors are involved in producing the allergic reaction and the autoimmune response. Again, the binding of complex carbohydrates to these receptor sites inhibit the reaction and/or response. Therefore, allergies, allergy-related diseases and autoimmune diseases respond to treatment by oral, mucosal, topical and parenteral administration of complex carbohydrates as described herein.

One of the most recent theories to explain the significant neurological degeneration that occurs in Alzheimer's Disease involves a substantial inflammatory component (SCIENCE, vol: 286, 17 Dec., 1999, pgs 2352-2355) which is concluded herein to be related to the adhesion cascade. Therefore, the present inventors have found that the complex carbohydrates of this invention can be used to prevent and/or treat Alzheimer's Disease. Another explanation for the development of dementia and Alzheimer's Disease is that an amyloid protein is produced in the brain resulting in the formation of amyloid plaques that lead to neuronal degeneration. The neuronal degradation is associated with diseases related to various types of dementia including but not limited to Alzheimer's Disease. Since it is known that CD44 is present in significant amounts on neuronal cells in the brain, the complex carbohydrates of the present invention bind to CD44 and/or other receptor sites in the brain and inhibit the formation of such amyloid plaques.

Accordingly, although not bound by any theory, the invention relates to a composition of matter comprising complex carbohydrates preferably as the sole active ingredient, applied topically, orally, mucosally or parenterally to prevent and treat diseases and conditions associated with allergies, autoimmunity, and the adhesion, metastatic or coronary cascades. However, the compositions described in U.S. Pat. No. 5,888,984 and in PCT/US00/02328 may also be utilized in the methods of the present invention.

Additionally, this invention describes a composition of matter comprising at least one complex carbohydrate and at least one transdermal or transmucosal carrier useful for effecting transdermal or transmucosal migration of said complex carbohydrate, resulting in topical or mucosal delivery of said molecules, through the skin or mucous membranes of mammals and into the bloodstream in order to prevent or treat the diseases and conditions associated with allergic reactions, the adhesion cascade the metastatic cascade or the coronary cascade. Transdermal carriers are those compounds that allow molecules, including macromolecules to pass through the skin and into the blood stream of mammals. Transmucosal carriers are those compounds that allow molecules including macromolecules to pass through the mucous membranes and into the blood stream of mammals. A patch or bandage can be embedded with the complex carbohydrates of the present invention so as to extend delivery of the molecules and/or provide slow release over several days. In the use of the complex carbohydrates of the present invention in bandages, they can be used without the presence of transdermal or transmucosal carriers with open wounds, or containing said carriers when used to treat closed wounds or reduce scarring or scar tissue.

This invention further describes a method of preventing and treating diseases and conditions of mammals associated with allergies, autoimmunity, the adhesion cascade, the metastatic cascade or the coronary cascade comprising administering a composition of complex carbohydrates topically, orally, mucosally or parenterally preferably on a repeated basis (e.g. 2 times per day, preferably 4 times per day, and most preferably 8 times per day, or simply "as needed").

Applications of the present invention would be made on a repeated basis for the term of the disease or condition or as long as necessary to prevent the diseases or condition from progressing, or to treat the diseases or conditions until they are resolved.

Finally, this invention describes a mechanism by which inflammation, including diseases and conditions associated therewith, tumor growth, tumor metastasis, allergies and allergy-related diseases, autoimmune diseases, coronary diseases and central nervous system diseases can be prevented or treated by administering complex carbohydrates topically, orally, mucosally, or parenterally.

It is understood that this invention describes the prevention and treatment of numerous diseases and conditions including but not limited to arthritis (osteoarthritis and rheumatoid arthritis), gastritis, stomach or intestinal ulcers, colitis, esophagitis, bronchitis, the common cold, rhinitis, sore throat, tonsillitis, tendonitis, fibromyalgia, chronic fatigue syndrome, interstitial cystitis, polymyositis, autism, Lupus Erythematosis, headaches including migraines, pancreatitis, anaphylaxis, vaginitis, hemorrhoids, sunburn, heat burns, temporomandibular joint (TMJ) condition, gingivitis, dental caries, dental pain, post surgical pain, menstrual pain, extremity cramps, pre and post partum pain, itching associated with allergies and hypersensitivity (e.g. poison ivy, oak and sumac and eczema), asthma, emphysema, Attention Deficit Disorder, Attention Deficit Hyperactivity Disorder (ADHD), fibromyalgia, Turret's Syndrome, Multiple Sclerosis, Amyotrophic Lateral Sclerosis (ALS) or Lou Gehrig's Disease, Parkinson's Disease, high blood pressure, heart disease, heart attack, vasculitis, stroke, increased degradation of spinal nerves post spinal cord injury, head or brain trauma post injury, adhesion formation post surgery or chemotherapy, scar formation post surgery, non-healing wounds, decubutis ulcers, irritation of nerve bundles (e.g. trigger points) ganglion formation, dementia including but not limited to Alzheimer's disease, Human Immunodeficiency Virus infection (HIV), yeast infections, bacterial infections, viral infections, encephalitis, epilepsy, meningitis, peripheral neuropathy, Creurtfeldt-Jacob Disease, Bell's Palsy, cognitive disorder, cancer, Diabetes, skin problems such as acne, lick granulomas, hot spots, psoriasis, rashes, wrinkles, and even hair loss.

Such prevention and treatment are accomplished by topically, orally, mucosally or parenterally applying complex carbohydrates of the present invention to mammals in an amount and number of applications so as to be effective in preventing and treating the target disease or condition. It is understood that such prevention or treatment results in blockage of receptor sites associated with allergies, autoimmune mechanisms, the adhesion cascade, metastatic cascade, or coronary cascade.

DETAILED DESCRIPTION OF THE INVENTION

This invention describes novel uses for a composition of matter comprising at least one complex carbohydrate that is applied topically, orally, mucosally or parenterally to prevent and/or treat diseases and conditions associated with allergies, autoimmunity, the adhesion cascade, the metastatic cascade or the coronary cascade. The invention also encompasses novel uses for a composition comprising at least one complex carbohydrate and at least one transdermal or transmucosal carrier. The invention also preferably encompasses novel uses for a composition of matter comprising complex carbohydrates as the sole active ingredient. Further, the compositions disclosed in U.S. Pat. No. 5,888,984 and in PCT/US00/02328 (including provisional applications 60/117,988 filed Feb. 1, 1999, 60/127,749 filed Apr. 6, 1999, 60/137,098 filed Jun. 2, 1999, 60/142,306 filed Jul. 3, 1999 and 60/166,326 filed Nov.

19, 1999 on which priority is based in PCT/US00/02328) may also be utilized in the methods of the present invention.

More specifically, the present invention is directed to a method of preventing and treating diseases and conditions associated with allergies, autoimmunity, the adhesion cascade, the metastatic cascade and the coronary cascade comprising administering said complex carbohydrates to the affected mammal topically, orally, mucosally or parenterally. A significant feature of this invention is that the complex carbohydrates are preferably administered in a low dose. By low dose is meant from 0.000001 mg/kg to 150 mg/kg, preferably from 0.001 mg/kg to 100 mg/kg and more preferably from 0.01 mg/kg to 20 mg/kg.

The invention also describes a method for reducing the sequelae of trauma in irritated or inflamed tissue of mammals by the topical or mucosal application of a mixture of a transdermal or transmucosal carrier and one or more complex carbohydrates or mixtures thereof. The composition described is applied directly on or over the traumatized site or on a mucous membrane.

Finally, the invention describes a method for reducing the sequelae of trauma in irritated or inflamed tissue of mammals by topical, oral, mucosal or parenteral application of a complex carbohydrate of the present invention or mixture thereof as the only active ingredient. By trauma is meant an event that produces an adverse effect on a mammal. By sequelae of trauma is meant the pain, swelling, inflammation, adhesion formation, nerve damage, nerve sensitivity and any other physiological change that results from trauma.

Many of the complex carbohydrates of the present invention are macromolecules. Macromolecules as used herein means any molecule with a molecular weight >1000 daltons (Da). Mammals as used herein includes but is not limited to humans, dogs, cats, horses, cattle, swine, rabbits, guinea pigs, mice. Topical administration as used herein means application to the dermis anywhere on the mammal, including into the ear canal. Mucosal administration as used herein means application to any mucous membrane of a mammal. Mucous membranes include but are not limited to the mouth, gums, nasal passage, throat, vagina and the rectum. Transdermal as used herein means transfer of molecules, including macromolecules through the skin of mammals so that the complex carbohydrates may act systemically. Transmucosal as used herein means transfer of molecules, including macromolecules through the mucous membranes of mammals so that the complex carbohydrates may act systemically.

Diseases preventable and treatable by the present invention include but are not limited to tonsillitis, the common cold, pancreatitis, ulcerative colitis, stomach or intestinal ulcers, cold sores, Lupus Erythematosis, Parkinson's Disease, osteoarthritis, degenerative arthritis, rheumatoid arthritis, polymyositis, Amyotrophic Lateral Sclerosis (ALS) or Lou Gehrig's Disease, multiple sclerosis, Creutzfeldt-Jakob Disease heart disease, heart attack, vasculitis, stroke, Alzheimer's disease, asthma, emphysema, allergy-related diseases, Human Immunodeficiency Virus (HIV) disease, yeast infections, bacterial infections, encephalitis, epilepsy, meningitis, peripheral neuropathy, Bell's Palsey, Cerebral Palsey, cancer and Diabetes. Conditions preventable and treatable by the above-described complex carbohydrates include but are not limited to ulcers, gastritis, esophagitis, bronchitis, sore throat, tendonitis, fibromyalgia, headaches including migraines, vaginitis, anaphylaxis, hemorrhoids, sunburn, heat burns, temporomandibular joint (TMJ) conditidn, dental caries, dental pain, gingivitis, post surgical pain, menstrual pain, cramps, pre and post partum pain, interstitial cystitis, itching associated with allergies and hypersensitivity (poison ivy), pain associated with insect bites or stings, Attention Deficit Disorder, Attention Deficit Hyperactivity Disorder (ADHD), Turret's Syndrome, plaque formation in arteries and veins, degradation of spinal nerves post spinal cord injury, head and brain trauma post injury, adhesion formation post surgery or post chemotherapy treatments, scar formation post surgery, wound healing, decubutis ulcers, irritation of nerve bundles (trigger points) ganglion formation, cognitive disorder, skin problems such as acne, eczema, lick granulomas, hot spots, psoriasis, rashes, wrinkles, and even hair loss.

Particularly amenable conditions or diseases targeted for such prevention or treatment include but are not limited to irritated or inflamed muscles, cramped muscles, inflamed tendons, inflamed nerves or nerve bundles (e.g. inflamed ganglion, lick granulomas, trigger points, fibromyalgia), swollen and painful joints, inflamed bladder (interstitial cystitis) bruised tissue, tired feet, allergic conditions of the skin, other allergic conditions (e.g. hot spots, psoriasis, asthma, ADD and ADHD), chronic fatigue syndrome, open wounds, decubitis ulcers, burns, sunburns, inflamed stomach or intestinal lining (gastritis, colitis, ulcers), dental problems, inflamed bronchi or esophagial lining, adhesions formed after surgery, trauma or chemotherapy, pain post surgery, dental work or injury, plaques formed on veins or arteries leading to heart disease and stroke, inflammation associated with Alzheimer's Disease, Multiple Sclerosis, amylotropic lateral sclerosis (ALS), head or brain trauma, degration of the spinal cord post spinal cord injury, tumor formation and tumor metastasis.

A significant advantage of this invention is that pharmaceutical grade complex carbohydrates are not required for topical, oral or mucosal application. The invention preferably uses cosmetic or food grade (e.g. low purity) complex carbohydrates for these applications. Such complex carbohydrates can be obtained from any source as long as the source is not contaminated with undesirable adventitious agents (disease-producing viruses, bacteria, fungi, parasites, etc.). Such low purity complex carbohydrates such as mucopolysaccharides may be contaminated with up to 20% wt/vol proteins, 15% wt/vol nucleic acids, 1% wt/vol teichoic acids, 5% wt/vol lipids, fractions of hyaluronic acid <30,000 (defined as reactive by both Balazs in U.S. Pat. No. 4,141,973 and della Valle in U.S. Pat. No. 5,166,331), 5% wt/vol endotoxins and other small molecules. They will cause reactions when injected into monkey eyes or joints of horses but will not cause reactions when applied to the skin of mammals or when delivered orally or mucosally to such mammals. Because the low purity pharmaceutical compositions of this invention are applied topically, orally or mucosally, these contaminants produce no adverse reactions (e.g. irritation or blistering of skin). Additionally, if one must select and use only certain molecular weight ranges of hyaluronic acid or salts thereof, the cost would be prohibitive. In fact, the presence of multiple molecular weight fractions in compositions of the immediate invention is preferable for efficacy.

In order to assure freedom from contaminating microorganisms, the formulations of this invention can include preservatives allowable in foods or topical preparations. Allowable preservatives include but are not limited to methyl and propyl parabens, propylene glycol, ethylenediamine tetraacetic acid (EDTA), sorbitol, ascorbic acid, sorbate and sorbic acid, benzoic acid, and any other acceptable preservative, including mixtures thereof.

All molecular weight ranges of complex carbohydrates are effective in formulations of this invention. For instance, complex carbohydrates with a molecular weight of <1,000, 1,000 to 30,000, 100,000-500,000, >1,000,000 or >4,000,000 have proven to be effective. It has been found that complex carbohydrates, especially glycosaminoglycans with lower molecular weights (e.g. <30,000) act more quickly than those with high molecular weights (e.g. >1,000,000). Indeed, for treatment of allergy-related diseases and autoimmune diseases or conditions, it is preferable to administer glycosaminoglycans, especially sodium hyaluronate, salts or derivatives thereof (also called hyaluronic acid or hyaluronan) with a molecular weight average below 300,000 Da. For inflammatory diseases, diseases or conditions related to the adhesion cascade, the metastatic cascade or the coronary cascade, the high molecular weight glycosaminoglycans provide a longer-lasting effect. The latter macromolecules are broken down by enzymes in the body (hyaluronidase) to smaller molecules that are active in binding or stimulate production of increased amounts of lower molecular weight hyaluronic acid by the mammals' own body. Therefore, there is a longer release of the more active smaller molecules producing a longer period of efficacy. Thus, the preferred formulation for most treatments includes a mixture of low and high molecular weight complex carbohydrates.

It has been noted by the inventors that the optimum molecular weight for treatment of allergies, allergy-related diseases and conditions, asthma, ADD and ADHD is between 30,000 and 500,000 Da, preferably between 100,000 and 300,000. It has been determined that very high molecular weight ($>4\times10^6$) is essentially ineffective for treatment of the above.

The complex carbohydrates useful in combination with transdermal or transmucosal carriers for direct topical or mucosal application on sites of trauma or to be absorbed therein, may be of any type already recognized as useful for parenteral treatment. Additionally, complex carbohydrates, including polysaccharides, glycosaminoglycans or their derivatives that bind to leukocyte receptor sites and/or bind to selectins, integrins, or any other receptor sites that are involved with the mechanisms by which leukocytes move to sites of trauma or that enable metastasis of tumors and that, when bound, serve to inhibit any of the steps of the adhesion cascade, allergy or autoimmune mechanisms, the metastatic cascade, or the coronary cascade would be useful in such pharmaceutical compositions. Such compounds may be obtained from any source. They can be extracted from rooster combs (U.S. Pat. No. 4,141,973), produced by fermentation of bacteria (U.S. Pat. No. 4,782,046), or extracted from trachea, skin, umbilical cords, etc. and need only be pure enough to be used as a cosmetic in that they do not cause reactions when administered topically, orally or mucosally. These molecules include but are not limited to polysaccharides, glycosaminoglycans such as hyaluronic acids and derivatives or salts thereof (Genzyme, Lifecore Biomedicals, Meiji Seika Kaisha, Ltd.), chondroitin sulfates A, B, or C or their derivatives (SIGMA Chemical Company), keratan sulfate and derivatives thereof (SIGMA Chemical Company), heparin or heparin sulfate and derivatives thereof (SIGMA Chemical Company, Rhone Poulenc Rorer Pharmaceuticals), dermatan sulfate and derivatives thereof (SIGMA Chemical Company) and certain sialylated sugars such as trifucosyllacto-N-hexaose and sialyl Lewis$^x$ (Oxford Glycosystems). The sources listed are exemplary only and not limitations of the invention.

The preferred complex carbohydrates of this invention are mucopolysaccharides (glycosaminoglycans) including hyaluronic acid and salts, sulfates or derivatives thereof, chondroitin sulfate and polysulfated forms, salts or derivatives thereof, sialyl Lewis$^x$ and salts or derivatives thereof, heparin and sulfates, salts or derivatives thereof, dermatan, and sulfates, salts or derivatives thereof, keratin and salts, sulfates and derivatives thereof, as well as combinations of the above. The most preferred complex carbohydrates are hyaluronic acid including salts, sulfates or derivatives thereof, chondroitin sulfate including polysulfated forms, low molecular weight heparin including salts, sulfates and derivatives thereof and sialyl Lewis$^x$ including salts and derivatives thereof and combinations thereof.

It is a preferred embodiment of this invention that at least two different molecular weight ranges of complex carbohydrates be included in the composition. At least one should be from a low molecular weight range {from 1000 to <50,000 (e.g. 49,000)} and the other one or more should be from a higher molecular weight range (from 100,000 to 500,000 or >1,000,000). Such complex carbohydrates may or may not be a mixture of two or more different types of complex carbohydrates. For instance, one complex carbohydrate providing the high molecular weight moiety could be selected from the group consisting of glycosaminoglycans such as hyaluronic acid and another complex carbohydrate in the same pharmaceutical composition providing the low molecular weight moiety could be a second polysaccharide or a sialylated sugar selected from the group consisting of chondroitin sulfate, keratan sulfate, heparin, heparin sulfate, dermatan sulfate, acemannan, sialyl Lewis$^x$, and hexaoses. When heparin is used, it is advantageous to use low molecular weight heparin as it has been demonstrated to be free of anti-coagulant activity. However, high molecular weight heparin will be broken down to low molecular weight heparin when administered orally or mucosally.

A more preferred embodiment of this invention comprises a mixture of at least two glycosaminoglycans. One of the glycosaminoglycans would be of a low molecular weight range (<30,000). The second glycosaminoglycan would be of a high molecular weight (>500,000 Da).

The most preferred embodiment of this invention comprises a mixture of two or more molecular weight ranges of hyaluronic acid or salts or derivatives thereof, such as sulfates, acetates, phosphates, methylates and nitrates. Said composition comprises for instance, a hyaluronic acid or salt or derivative thereof with a molecular weight of <100,000 Da combined with a hyaluronic acid or salt or derivative thereof which has a molecular weight >1,000,000 Da.

Routes of administration of the complex carbohydrates of the present invention include parenteral (discussed below), topical whereby the compounds may or may not be combined with transdermal carriers including but not limited to essential oils; oral whereby the compounds may or may not be mixed with transmucosal carriers including but not limited to essential oils or other transmucosal carriers, coated with protective oral delivery materials such as hydrogels, carbopols, etc., or delivered orally without a coating wherein the complex carbohydrates are the sole active ingredient, mucosally wherein the complex carbohydrates are the sole active ingredients or parenterally. For purposes of this invention, mucosal delivery includes but is not limited to application of the compounds to the mucous membranes of the nose, eyes, mouth, throat, gums, tonsils, eyes, esophagus, stomach, colon, rectum, vagina, or any other mucous membrane.

It should be understood that complex carbohydrates used for parenteral administration to mammals must be pure enough to be injected safely without causing adverse local or systemic effects and of a viscosity allowing ease of injection. The preferred viscosity is that which is safe to administer without stimulating an adverse effect in a mammal. The intravenous route would require a lower viscosity than other parenteral routes of administration. For instance, a viscosity of 500 centipois should not cause problems. A preferred viscosity is less than 200 centipois. In the case of parenteral injections, especially those administered IV, pharmaceutical grade complex carbohydrates may be necessary. Parenteral injections may be administered intramuscularly (IM), intravenously IV), subcutaneously (SC), intradermally (ID), intraparitoneally (IP) and/or injected into tumors.

The parenteral formulation of the present invention may be in an aqueous form as a liquid or gel that is safe when injected IM, SC, IV, ID, IP, or by any other route of administration. This formulation must be purer and be of a pharmaceutical grade. By a pharmaceutical grade is meant that it should be sterile, contain <3% protein (w/w), <5 μg/mL nucleic acids as measured by UV absorbance at 260 nm, <0.5 EU/mL endotoxin as measured by LAL, <80 ppm (w/w) iron and <1.0 ppm heavy metals. The most effective injectable formulation would contain mucopolysaccharides or glycosaminoglycans, more specifically, low molecular weight heparin, hyaluronic acid of all molecular weights, chondroitin sulfate, dermatan sulfate and/or keratin sulfate. If hyaluronic acid is used, the viscosity must be at a level acceptable to be injected by the route chosen without causing adverse reactions. For instance, high viscosity hyaluronic acid >1000 centipoise would not be injected intravenously whereas it could be injected subcutaneously or intramuscularly. Low viscosity hyaluronic acid <500 centipoise could be injected intravenously, subcutaneously or intramuscularly.

Administration of complex carbohydrates by the parenteral routes of administration has been found to be particularly effective in the treatment of any type of inflammation, pain, nerve damage, nerve sensitivity, autoimmunity and/or itching which is associated with the adhesion cascade, tumors associated with the metastatic cascade and development of heart diseases and stroke associated with the coronary cascade described earlier. This route of administration is preferable for treatment of pain post surgery or dental procedures, treatment for various types of cancer wherein patients cannot ingest food or liquids, treatment of degenerative muscle and joint diseases including the treatment of Multiple Sclerosis, ALS, osteoarthritis, rheumatoid arthritis, or post partum pain. It is also useful for treatment of spinal cord injuries, treatment of heart attacks and stroke (e.g. heart disease due to high blood pressure and stroke), treatment of pain and swelling and/or fractures resulting from athletic injuries, treatment of inflammation and pain associated with bursitis, reduction of inflammation (edema) in extremities resulting from diabetes, reduction of inflammation and pain in association with interstitial cystitis, treatment of decubitus ulcers resulting from poor circulation by diabetic patients or bedridden patients, treatment of inflammation and itching of skin resulting from severe allergic reactions such as poison ivy and insect bites/stings, treatment of sever ADD, ADHD or autism, treatment of anaphylaxis, treatment of polymyositis, treatment of inflammation and pain associated with tendonitis, treatment of inflammatory skin conditions such as severe acne or psoriasis and treatment of burns or sunburn. In severe situations, treatment may include both parenteral injection and oral, mucosal or topical application of one or more complex carbohydrates.

As indicated earlier, the most recent theories to explain heart attacks and stroke involves the eruption of unstable plaques which have been found to be infiltrated with T-cells and macrophages thus linking these disease syndromes to the adhesion cascade. Thus, the present inventors have determined that heart disease (high blood pressure, heart attacks and stroke) can be treated with the complex carbohydrates of this invention. Further, hyaluronic acid, chondroitin sulfate, heparin sulfate, low molecular weight heparin, keratin sulfate or dermatan sulfate, including salts or derivatives thereof can be taken daily as a preventative for heart disease and stroke. Preferably, amounts from 1 mg/day to 20 mg/day are used to prevent heart disease and stroke. This could be administered orally or mucosally. Acute disease, including heart attacks could be treated by parenteral injection of the complex carbohydrates of the present invention. Alternately, a mixture of hyaluronic acid and chondroitin sulfate could be administered daily for prevention of heart disease and stroke. Again, the daily dose would preferably be less than a total of 100 mg. Repeated low doses have been demonstrated to be between 0.0001 mg and 100 mg.

For topical, oral and mucosal deliver, transdermal or transmucosal carriers can be added to enhance the penetration of the complex carbohydrates through the skin or mucous membranes. Transdermal and transmucosal carriers include but are not limited to essential oils, polymer blends containing low density polyethylene copolymer or ethylene and 1-butene, 1-hexene, or 1-octene and a linear low density polyethylene copolymer, chemical esters, salicylates, dimethyl sulfoxide (DMSO) and glycocholates. It is preferred that very low concentrations of essential oils be used to orally or mucosally deliver the complex carbohydrates of the present invention, including the macromolecules, through mucous membranes and, consequently, into the blood stream. By very low concentration of essential oils for use in mucosal or parenteral administration is meant that the essential oil is added to a concentration in an amount from 0.00001% to no more than 1%, preferably, no more than 0.01%, more preferably no more than 0.005%. Therefore, concentrations of essential oils around 0.00001% and 0.005% are preferred for transmucosal delivery.

Transdermal formulations of the present invention utilize slightly higher concentrations of essential oils. These range from 0.05% to 5.0%, preferably from 0.5% to 3.0%.

The essential oils of the present invention may be either natural or synthetic and may be obtained from any source. For instance, natural Eucalyptus Oil, Rosemary Oil, Pine Needle Oil, Tea Tree Oil, Sage Oil, Jojoba Oil, Cinnamon Oil, Anise Oil, Lemon Oil, Lime Oil, Orange Oil, Peppermint Oil, Spearmint Oil, Wintergreen Oil, Clove Leaf Oil, Almond Oil, White Pine Oil, Camphor Oil, Cardamon Oil, Cedar Leaf Oil, Sweet Birch Oil and many others can be purchased from Lorrann Oils. Synthetic Wintergreen Oil, Anise Oil, Fir Tree Oil, Rose Oil and Camphor Oil can be obtained from the same source. Menthol and derivatives thereof can be obtained from SIGMA Chemical Company. The purity of these essential oils is of little concern as long as they meet the requirements for a food or cosmetic and do not produce adverse reactions when applied to the skin of mammals. An example of an animal-derived essential oil is EMU oil, extracted from the skin of the EMU.

The formulation of a complex carbohydrate with a natural or synthetic essential oil should be adequate to form an emulsion, suspension, solution, cream or ointment at the time of application. A liquid formulation will not be effective if the oil is separated from the aqueous phase. However, a suspension or solution that may be resuspended by shaking prior to application is acceptable for use. Any cream or ointment base that does not interfere with the effectiveness of the active ingredients may be included in the formulation. Therefore, one embodiment of this invention is a cream base containing at least one complex carbohydrate and at least one essential oil. Another embodiment is an ointment base containing at least one complex carbohydrate and at least one essential oil. One preferred embodiment is a liquid or gel formulation in an aqueous base that contains at least one complex carbohydrate and at least one essential oil. A significant advantage of this liquid formulation is that the preparation is not greasy or oily, does not leave a greasy or oily film on the skin and does not leave a lingering odor on the skin. The most preferred embodiment is a liquid or gel formulation in an aqueous base that contains at least one complex carbohydrate as the sole active ingredient.

The complex carbohydrates of the present invention can also be prepared as a solid and incorporated into bandages. Preferably a 1% solution is used. It can be embedded into the bandage material remaining moist, or dried. It can also be formulated into a solid polymer by addition of cross-linking agents. The latter may be applied to open wounds or to scars to assist with the healing process and/or reduce scar formation.

The treatment of irritated or inflamed mammalian tissue by direct topical application requires a dose or total dose regimen effective to reduce or alleviate the results of the trauma. It is preferred to administer at least about 0.000001 mg/Kg of body weight of each ingredient over the site of trauma at least once per day or as often as necessary. The components of this formulation are naturally-occurring substances and are safe when applied topically. There is no inherent upper limit to the tolerable dose. However, as in all medicinal treatments it is prudent to use no more than is necessary to achieve the desired effect. It has been noted that more intense inflammation and pain require more dose applications for relief. A dose of 100 mg/Kg of body weight has been used safely and could serve as an upper limit for use. Similar dose regimens are recommended for wound healing whereas the pharmaceutical composition is applied on the wound until adequate promotion of granulation of the wound has occurred and healing is complete.

A convenient topical application formulation is a combination of one or more complex carbohydrates such as polysaccharides, oligosaccharides, or glycosaminoglycans at a total concentration of between 0.1% and 5% wt/vol. These can be used without a transdermal carrier or with a transdermal carrier including one or more essential oils. If essential oils are used, they are preferably combined with the complex carbohydrates at a total concentration of between 0.5% and 20% vol/vol with the remainder of the formulation being made up of a liquid, cream or ointment base. The liquid base may be aqueous.

A preferred embodiment of the topical formulation is a combination of one or more glycosaminoglycans at a total concentration of between 0.1% and 5% wt/vol with one or more essential oils at a total concentration of between 0.5% and 5% vol/vol with the remainder of the formulation being a cream, ointment or aqueous base.

A more preferred embodiment of the invention is a combination of equal amounts of two or more molecular weight ranges of glycosaminoglycans (one below 30,000 and one above 500,000) at a combined concentration of between 0.5% and 3.0% wt/vol with two or more essential oils having a total concentration of between 0.5% and 5.0% vol/vol with the remainder of the formulation being an aqueous, cream or ointment base.

The most preferred embodiment of the topical formulation is a combination of hyaluronic acid (sodium hyaluronate or hyaluronan) with a molecular weight <30,000 with hyaluronic acid with a molecular weight between 100,000 and 500,000 or >750,000 at a total hyaluronic acid concentration of between 0.5% and 3.0% wt/vol and an essential oil selected from the group comprising Rosemary Oil, Tea Tree Oil, Wintergreen Oil, Eucalyptus Oil, Menthol and Camphor at a concentration of between 1.0% and 3.0% vol/vol with the remainder of the formulation being DI water.

Preferred complex carbohydrates include heparin, preferably low molecular weight, hyaluronic acid, chondroitin sulfate, dermatan sulfate, keratan sulfate, and acemannan (active ingredient of Aloe Vera).

Preferred essential oils include Tea Tree Oil, Rosemary Oil, Eucalyptus Oil, Wintergreen Oil, Sage Oil, Jojoba Oil, White Pine Oil, Camphor Oil, Cinnamon oil, Oil of Clove, Spearmint Oil, Peppermint Oil, EMU Oil and Menthol.

The oral and mucosal formulations of the present invention include any of the complex carbohydrates listed above, alone or in combinations, whereby the formulation is administered as a form selected from the group consisting of a liquid, an emulsion, a suspension, a cream, an ointment, a gel, a foam, a spray, a solid, a powder and a gum. It is contemplated that the liquid or solid could be added to a drink or drink mix, to food, be a part of a soft drink or any other type of carbonated drink, a supplement drink, used as a mouthwash, or added to a mouthwash, as a toothpaste, as a gargle, as a spray, added to a vaporizer, as a liquid center of a gum or throat lozenge, added to a food, cookie or treat, or used in any other way so as to retain the effectiveness of the complex carbohydrate. A gel form can include a gel applied by mouth, to the gums, to the tongue, under the tongue, to the eyes, to the nose, to the vaginal area or vagina, or to the rectum. A foam could be added to wounds, to the mouth, to the gums, to the vagina or any other mucous membrane. A solid can be incorporated into food, treats such as candy or treats for animals, a chewing gum, a dissolvable gum, a lozenge, capsules, tablets, dissolvable tablets, suppositories, a bandage and any other form that would not damage the effectiveness of the complex carbohydrates or the essential oils, if used in the formulation. Other additives may be added to said oral formulations to improve taste and palatability or enhance the flavor. For instance, treats for horses may include sugar, flavorings such as apple or peppermint or a liquid or gel may be applied to a sugar cube, food or other treat. Treats for dogs may include liver, apple, peppermint, yeast or any other palatable flavoring.

The same formulations as mentioned for oral use can be used for mucosal delivery of the complex carbohydrates. The only limitation is that the formulation remain in contact with a mucosal surface for a period of at least 2 to 10 seconds.

Although the complex carbohydrates may be added to foods that are then baked, it is preferred to add the complex carbohydrates to the surface of the food after baking is complete. This retains the greatest activity.

It is contemplated that the complex carbohydrates of the present invention may be added to nutritional supplements to enhance their effectiveness. For instance, a mixture of complex carbohydrates and zinc, zinc gluconate, zinc gluconate glycine could be used for more effective treatment of sore throat and colds. A mixture of the complex carbohydrates of this invention and capsicum may produce an even more effective treatment for joint pain and swelling. Addition of vitamins, minerals and other nutritional additives may produce enhancement of the nutritional activity by the complex carbohydrates.

The most recent theory to explain the significant neurological degeneration that occurs in Alzheimer's Disease involves a substantial inflammatory component (SCIENCE, vol: 286, 17 Dec., 1999, pgs 2352-2355) which appears to be related to the Adhesion cascade. Therefore, the present inventors have determined that the complex carbohydrates of this invention can be used to prevent and/or treat Alzheimer's Disease. For example, it is contemplated that hyaluronic acid, salts or derivatives thereof could be administered daily as a preventative for Alzheimer's Disease. Amounts from 1 mg/day to 20 mg/day should prevent the degradation apparent in Alzheimer's Disease. This could be taken orally. Preferably, it would be taken mucosally. Acute Alzheimer's Disease could be treated by parenteral injection. Alternately, a mixture of hyaluronic acid and chondroitin sulfate could be administered daily for prevention or treatment of Alzheimer's Disease. Again, the daily dose would preferably be less than a total of 100 mg.

The significant neurological degeneration that occurs after spinal cord injuries leading to irreparable paralysis, is attack by the leukocytes rushing to the site of trauma (via the mechanism of the adhesion cascade) to help repair the traumatized area, but instead, degrading the ends of the nerves in the spinal cord, fraying them which effectively inhibits their potential realignment and partial or complete repair. Paralysis resulting from spinal cord injuries may be prevented or treated effectively using the complex carbohydrates of this invention. In this case, since the patient may not be able to take an oral medication, the medication may be administered mucosally using suppositories (rectal or vaginal) or parenterally, injecting IM, SC, or delivering IV. The dose may need to be higher, in the range of 20 to 1,000 mg per day. Drugs to assist repair of nerves would preferably be administered concurrently.

The invention is further illustrated but is not intended to be limited by the following examples.

Example 1

An 18 year old female suffered from chronic fibromyalgia localized in the face and neck. This condition had existed for approximately 5 years. There was nothing that provided relief for her condition. Prior to use of the compositions of the present invention, she had taken pain relievers, acupuncture, and numerous other procedures to treat her condition. Nothing had provided substantial relief without severe side effects. She was given a formulation containing a mixture of high and low molecular weight 1% sodium hyaluronate. This formulation was prepared from hyaluronic acid powder obtained from Collaborative Laboratories, Inc. which was made up to a 1% solution in deionized, distilled water. One half of the final 1% solution was removed and its molecular weight was broken down by alkaline hydrolysis. The pH was adjusted to between 11 and 14 using 10N NaOH. Then the solution was heated while mixing at a temperature between 37° and 50° C. When a molecular weight of between 10,000 and 50,000 was obtained as measured by viscosity (Brookfield Viscometer), the pH was adjusted back to neutral (between 6.0 and 7.0). The final mixture was then prepared by combining 1 liter of this low molecular weight preparation with 1 liter of the original 1% solution (high molecular weight of >1×10$^6$) of sodium hyaluronate. The patient was instructed to take this formulation orally, holding the liquid in the mouth for several seconds to allow mucosal adsorption before swallowing it. She took 10 mg two times per day (AM and PM). This represented a dose of approximately 0.2 mg/Kg. She reported that after only 1 day, her symptoms were greatly improved. After one week of daily use, she reported essentially no pain. She has continued to take the same dose for 6 months and has reported no return of her fibromyalgia as long as she takes the formulation. Therefore, a condition that has historically remained untreatable, and which appears to be related to the adhesion cascade and, perhaps, to allergies has been shown to be treatable with the compositions of the present invention.

Example 2

A 9 year old male suffering from severe Attention Deficit Hyperactivity Disorder (ADHD) complicated by Turret's Syndrome, who was being treated by diet control with little success, was given a sample of the mixture used in EXAMPLE 1. This treatment was not complicated by concurrent treatment with drugs such as Ritalin as his parents were adverse to using this medication. Therefore, any response observed was related to the use of the complex carbohydrates of the present invention. He took 10 mg in the morning and 10 mg in the evening, using the solution as a mouthwash (holding it in his mouth for about 10 to 20 seconds and then swallowing). His parents kept very strict records of his activity and noted that his Turret's Syndrome was fully controlled and he suffered no tics while taking the sodium hyaluronate. The one day that he forgot to take his morning dose he had a recurrence of his tics and became almost uncontrollable. However, within 15 minutes of his receiving the missing dose, he became calm and returned to normal. This boy has remained totally under control for 6 months. This had never been observed before, even when he was taking Ritalin. He had discontinued taking Ritalin 1.5 year before because of problems with side effects. The sodium hyaluronate provided no adverse reactions or side effects. It has been concluded that a disease typically thought to be related to a nervous disorder or to allergies was treatable by the complex carbohydrates of the present invention.

Example 3

A 60 year old male and 55 year old female (brother and sister) who routinely suffered severe sunburns the first few times that they were in the sun each summer, had been taking oral sodium hyaluronate gel for treatment of pain associated with a cervical disc stenosis (male) and chronic osteoarthritis of both knees (female). Pain from the conditions being treated was totally controlled by taking 5-10 mg twice per day. This dose represented 0.14 and 0.18 mg/Kg respectively. The sodium hyaluronate gel was prepared by adding sodium hyaluronate (Collaborative Laboratories, Inc) to deionized, distilled water to a 1% concentration. Preservatives selected from methyl paraben (0.17%), propylparaben (0.025%) and propylene glycol (10%) were added to maintain sterility of the liquid preparation. The pH of this preparation was between 6 and 8 and the preparation had a molecular weight of >1,000,000. The gel was being applied directly on the tongue by dropper bottle. Both went on vacation together and spent most of 5 days in the bright sun in a boat. They did not use a sun blocker. Each previous year both had suffered severe discomfort from sunburn after the first day's exposure. This time, at the end of the 5 days, both noted that they were not sunburned, had suffered no discomfort and were developing a nice tan. It is concluded that the preparation of this invention prevented sunburn, allowing tanning to occur. Additionally, it was noted that the formulation of this invention was able to control the pain associated with cervical disc degeneration and osteoarthritis. All such conditions are associated with the adhesion cascade, confirming that diseases and conditions associated therewith are preventable or treatable by the complex carbohydrates of the present invention.

Example 4

A 60 year old male suffering from colon cancer had been unable to tolerate his colostomy and demanded that his surgeon remove the colostomy and reconnect his colon. He refused chemotherapy. He was given a formulation of 1% sodium hyaluronate (Collaborative Laboratories, Inc) which was prepared with a mixture of molecular weights of hyaluronate (as described in EXAMPLE 1). When he began taking the hyaluronate preparation, his CEA was 70.1. He has taken the hyaluronate at a dose of 10 mg three times per day mucosally and after 6 months of treatment his CEA has dropped to 4.1. He has taken no other treatments. This patient had also suffered from polymyositis for approximately 15 years. For this condition he was taking 50 mg of Prednisone daily with little relief. He reported that after 1 week of taking the hyaluronate preparation of the present invention, he felt significant relief from the pain caused by his polymyositis. After 6 months of treatment with hyaluronate, he has been able to reduce his Prednisone to 5 mg every other day. His physician has reported that his polymyositis has gone into remission. This treatment of cancer demonstrates the successful use of the complex carbohydrates of the present invention to treat a disease associated with the metatastic cascade. The polymyositis that was successfully treated in this example was thought to represent treatment of a disease associated with the adhesion cascade or autoimmune disease.

Example 5

The subject adult was a 48 year old female who had suffered all her life with attention deficit disorder (ADD).

She never knew what her problem was until recently when she was diagnosed. She described her childhood as unfocused and explained that she felt as though she was in a constant mental fog—unable to think clearly, or for that matter, unable to focus on a thought at all. She found that she had allergies to almost everything including most foods (dairy products, wheat and corn, sugar, corn syrup, etc.) and most environmental inhalants, the worst being mold. Exposure to only a few minutes in a moldy room caused this individual to become dazed, unable to think, focus or even stay awake. She had only been able to do menial jobs. She spent most of her time staring out the window with no thoughts in her mind and, even if she tried, could not focus on a thought or task. She described herself as believing all her life that she was just stupid and unable to learn. She had been to multiple physicians and psychiatrists seeking treatment with no success. She had taken Ritalin with little relief. It allowed her to function partially but she was always tired and unable to focus on anything but the simplest of tasks. She agreed to take the oral sodium hyaluronate product and her family would report how she reacted. She did not believe that she could record her own responses because she was unable to concentrate long enough for such a task. She was initially provided low molecular weight sodium hyaluronate (<30,000), prepared as described in EXAMPLE 1. She began by taking 20 mg 3 to 4 times per day. Within five days of the start of treatment, she reported that she could focus enough to write a note about how she felt each day. As she was on the instant composition longer, her notes became more coherent and within about 10 days she was able to determine exactly which foods caused her the most problems and which environmental exposures caused the major difficulty. She discovered that various types of foods were actually producing her "mental fog" reaction, an anger reaction, welts on her face and neck and even anaphylaxis. After 30 days of taking the sodium hyaluronate oral formulation, she described her response as follows: "Before starting the oral formulation, I was in a continual state of feeling tired, foggy, feeling cold, having rashes and welts all over, and having a 'tight head'. I couldn't function well enough to drive or hold any type of job. I now believe that I know what a normal person must feel like. I'm having longer periods of well being, energy and clear thinking. Each week I have seen a progression of positive responses. This is the first time I have been able to define periods of allergic reaction. I can observe when reactions start and end. I'm not using nasal spray (Flonase) in the morning when I wake up or, especially before I go to bed. Before starting the oral formulation, I had to use this spray before bedtime or I would wake up in the middle of the night, coughing and choking with a lot of phlegm. I am able to start and finish projects. I have even been able to work crossword puzzles—something that I could never even look at prior to treatment. My quality of life is far superior than ever before. I have been offered a real job at an advertising agency. I feel like I can handle the job and do not get frustrated and spacey. I am also able to drive a car— something that I haven't done for at least 15 years."

FIG. 1 plots the response of this patient while taking the compositions of the present invention. It is based on the patient's own description of her average daily activities and reactions. The scale runs from a −30 (a reaction in which the patient responded in a manner wherein she was unable to function or focus on any activity) to +30 (energy, clear-thinking, able to focus, feel great). If there were no significant negative or positive responses during a day, the reaction rate was recorded as 0. The graph clearly demonstrates that the oral glycosaminoglycan (sodium hyaluronate) improved this patient's quality of life and reduced the reactions (after eating or exposure to environmental reactants). Toward the latter part of treatment, this patient was provided with a high molecular weight (>1,000.000) oral hyaluronate formulation. Her family reported an immediate lack of response that continued during the time when she continued to take this formulation. She was unable to work or drive a car during this period of time. After 9 days on the high molecular weight formulation she was switched to a formulation that contained a mixture of molecular weights of hyaluronate (as described in EXAMPLE 1). This formulation was prepared by mixing 3 parts of low molecular weight (<30,000) with 1 part of high molecular weight (>1,000,000). She demonstrated an immediate positive response that has continued. She has reported that whereas while taking the low molecular weight hyaluronate she felt extremely energetic and capable of doing anything and everything, when she ate or was exposed to something that caused her significant problems, she suffered from extreme "crashes". These "crashes" were observed by the inventor and would be described as a catatonic state in which this patient did not respond. She sat and stared into space or fell asleep. While taking the mixed molecular weight hyaluronate, she was not experiencing "highs" or "crashes". Instead, she maintained a feeling of focus, felt good and was capable of completing her work and family tasks as she thought a normal person would do. As can be observed in the graph in FIG. 1, when the low molecular weight sodium hyaluronate was replaced with high molecular weight sodium hyaluronate (without the patient's knowledge) the patient reported a total lack of efficacy. When she was placed back on the mixed molecular weight preparation, she returned to a state where she was functioning well, had excess energy and was able to focus. This individual has now periodically replaced the sodium hyaluronate with liquid 5% chondroitin sulfate. The positive response continued while taking this low dose chondroitin sulfate.

Example 6

The patient from EXAMPLE 5 did experience 2 anaphylactic reactions after eating certain foods containing corn syrup or being exposed to mold. During such reactions she would become catatonic and collapse. After the first such reaction, a pharmaceutical grade low molecular weight sodium hyaluronate (approximately 350,000 MW) was administered intramuscularly. She was observed for her response. Within 10 minutes she became conscious and was able to speak haltingly. She was unable to focus well on the conversation. Within 30 minutes she appeared normal and was able to carry on a coherent, intelligent conversation. She had no idea what had happened.

When a similar anaphylactic reaction occurred at a later date, it was decided to treat with oral hyaluronate. She again was catatonic and unconscious. Approximately 1 mL of low molecular weight (<30,000) sodium hyaluronate was applied under her tongue and around her gums. This treatment brought an initial response of consciousness within 30 minutes. Halting speech without the ability to focus occurred by 45 minutes post treatment. By 60 minutes post treatment she was able to carry on a focused conversation and appeared normal. This demonstrates that a glycosaminoglycan such as hyaluronate can be used to treat anaphylaxis when administered either parenterally or orally/mucosally.

Example 7

The subject child was a 9 year old male who has suffered with ADHD all his life. He had demonstrated learning disabilities compounded with behavioral problems. He was described as unable to focus, did not read, write or draw. Additionally, his behavior was such that he could not socialize with other children or with adults. When in contact with other children he was unable to play, often became angered and caused physical harm to others. He had been under treatment by several physicians, psychologists and allergists all his life but none were able to help his condition. The allergists determined that he had allergies to most all foods, dust, molds, soaps and just about everything in his environment. At one time he was prescribed Ritalin daily. However, while taking this drug he suffered hallucinations and became even more uncontrollable. At the time that he began treatment according to the present invention, the physician who was treating him was convinced that his ADHD was related to his severe allergies. Eating a certain food, such as corn, immediately produced anger and rage in this child. Similar responses were noted after eating or being exposed to other foods or mold.

This boy attended a special school in which his Teachers reported his daily activity to his parents so that they could try to monitor his eating habits. They provided a daily numerical score. A score of 100 was excellent. This child averaged daily scores of 0 to 10, at best. This child was placed on the low molecular weight oral glycosaminoglycan, sodium hyaluronate. A dose of 20-30 mg BID was applied orally in food or drinks. It was added to rice milk for breakfast and made into icing for cookies for snacks as he was not cooperative enough to take it on his own. His response was monitored by using the numerical score provided by his teachers and averaging it with a numerical score of his behavior at home provided by his parents. The child responded positively within a few days. The average scores plotted in FIG. 2, ranged from −40 to +40. Normal non-aggressive behavior was given a score of 0. The teachers at school were not informed of this treatment. Within 5 days of beginning treatment the comments from his teachers were: "He appears happy, having a good time but needs direction. Awesome day. Plays well with classmates. Helps other children who are having problems". His parents have commented that he has awakened in the morning and is happy, cheerful and cooperative in getting ready for school. This is something that they had not experienced in the past. He has suffered no adverse reactions from taking the complex carbohydrates of the present invention. FIG. 2 shows the response of this child to oral low molecular weight hyaluronic acid. The y axis is a numerical analysis of this child's ability to cooperate with other children and adults. If his behavior was belligerent, bossy, angry or non-cooperative he was scored as a −40 for the day. If his reactions to foods or environmental stimuli produced such a response it was recorded as a −40. If he responded as a normal 9 year old, the score was recorded as 0. If he responded extraordinarily well, helping other children, reading quietly, drawing or writing, he was given a score of +40. It was quite surprising that this child responded almost immediately becoming "a different child". His parents had thought that he did not know how to read, write or draw. Almost automatically, he requested books from the library and began reading quietly, he began drawing very intricate drawings and writing poems and stories. He also began preparing very elaborate meals for his parents (without any assistance). FIG. 2 demonstrates this superior behavior quite well. It also demonstrates that when treatment was stopped for approximately 2 weeks, there was a reversion to his original non-cooperative behavior. Upon restarting the treatment his behavior improved dramatically. It is thus clear that the glycosaminoglycans of the present invention can treat ADHD very effectively. Any route of administration may produce similar effects. In the most severe cases, the treatment would begin with a parenteral injection followed by oral or mucosal daily doses.

Example 8

The patient was a 37 year old female who had suffered from interstitial cystitis for eight years. She had seen many doctors and been to Mayo Clinic to seek treatment that could provide her with relief. This condition presents as a constant pain in the bladder that produces "excruciating pain" and a sensation of an intense need to urinate (urgency). It appears to be caused by inflammation of the lining of the bladder. Cysts or sores develop that are irritated by the urine in the bladder. Since the bladder cannot empty, there is constant irritation and constant pain. A recent theory is that the irritation is produced by allergic reactions to certain foods or drinks and by sexual intercourse. This patient had been to all types of physicians and even to the Mayo Clinic to obtain relief from her pain. She had been taking 100 mg per day of macrodantin and 20 mg per day of feldene that caused severe side effects. Additionally, she had taken 200 mg TID of Elmiron to reduce the inflammation in the bladder lining. This did not help. In order to sleep she took Prosed/DS, Ultram, Hydroxyzine HCl, Cardura, Amitriptyline. Sometimes all were taken at some time during the day or night. Even this regimen was unable to treat the pain. This patient was supplied with the mixed molecular weight preparation of sodium hyaluronate as described in EXAMPLE 1. She was also supplied with a topical preparation containing 1% wt/vol. Sodium hyaluronate at a molecular weight of <30,000 combined with 1% Oil of Wintergreen, 0.5% Spearmint Oil and 0.2% Peppermint Oil. She took 10 mg of the oral preparation 4 times per day. The last dose was taken before going to bed. Additionally, at bedtime, she rubbed her lower abdomen (over the bladder) with the topical preparation. She reported that she was able to sleep at least 6-7 hours without pain and without the need to get up to urinate. Within a week after starting this treatment she was able to discontinue all other medications. Now, all she requires is 1-2 Tylenol plus the sodium hyaluronate preparation of the present invention and she has continued to remain pain free. This demonstrates that inflammation, even in the bladder where the sodium hyaluronate does not penetrate, can be successfully treated with the compositions of the present invention. The additional fact that the topical preparation provided "an extra bonus of immediate relief" indicates that the topical use of the compositions of the present invention are extremely effective in treating extreme pain. It is proposed that the allergic reactions that stimulate this condition were successfully treated to relieve the constant irritation of the bladder.

Example 9

A 49 year old female who was diagnosed with Lupus Erythematosis 24 years ago, presented with an acute outbreak of the disease. Her face was covered with eruptions as was the skin on her forearms. She was also feeling very tired and complained of general joint pain. She was provided with a sodium hyaluronate preparation with a molecular weight of <30,000. She was instructed to initially take 10 to 20 mg of the liquid TID. She reported that after taking the first dose, the eruptions on her face began "drying up". By the third dose the eruptions were significantly reduced and beginning to heal. Within 3 days, the eruptions had essentially disappeared. This patient has been treated with the composition of the present invention for a period of 8 months without a recrudescence of the disease. She also reported that the constant aching and pain in her joints had disappeared and she felt 100% improvement.

Lupus Erythematosis is known to be an autoimmune disease. Therefore, the complex carbohydrate compositions of the present are able to successfully treat said autoimmune disease.

Example 10

An 80 years old female had been diagnosed with ovarian cancer that had spread to the lungs, liver and spleen. She refused chemotherapy. She was told that she had 3 weeks at most to live. She was provided treatment with the complex carbohydrate compositions of the present invention. When first provided with oral/mucosal sodium hyaluronate of mixed molecular weights (prepared according to the methods described in EXAMPLE 1), she had not eaten in 6 months and was unable to keep anything down, she was in extreme discomfort from extensive build up of fluids in the abdomen and chest and pain in the legs and feet which were extremely swollen. She was on an IV solution to restore fluids since she could not drink liquids. She was instructed to place as much as possible of the oral preparation in her mouth and let it absorb under her tongue. This was to be repeated as often as possible. Within 2 weeks she was able to eat small amounts of food. At this time, she received injections of 10 mg doses of sodium hyaluronate three times per week. Her condition continued to improve. As of this writing, she continues to improve, eats better each day and has survived for 4 months. She has received no chemotherapy and no other treatments. She indicates that she feels stronger each day and has been able to begin sitting in a chair and standing up. She has indicated that she has no pain since beginning to take the oral complex carbohydrates of the present invention. This demonstrates that even a terminal cancer patient who was near death can respond to treatment with the complex carbohydrate compositions of the present invention.

Example 11

A 38 year old male had suffered from high blood pressure most of his adult life. He had tried taking numerous drugs to treat his condition with little to no success. He agreed to try a complex carbohydrate of this invention to determine whether it might have a positive effect. He was supplied with a 1% solution of sodium hyaluronate formulation with a molecular weight range between 10,000 and 50,000. He took 10 mg in the morning and 10 mg in the evening. Sometimes he supplemented with a 10 mg dose after lunch if he was having a particularly stressful day. The patient's weight was 163 lbs. Therefore, each dose was 0.06 mg/Kg. Table 1 shows the results. The patient's blood pressure ranged around 160/115 prior to treatment. Within three days of starting treatment his blood pressure was dropping. By one week post initiation of treatment, his blood pressure was within the normal range. It has remained well within the normal range for six months during treatment with the complex carbohydrates of this invention. It is evident that high blood pressure can be effectively treated with the complex carbohydrate formulations of the present invention.

TABLE 1

Treatment of High Blood Pressure with Sodium Hyaluronate

| Day | BP Prior to medication | BP 5 min Post medication | BP 1 hours post medication | BP 2 hours post medication |
|---|---|---|---|---|
| −3 | 168/121 | N/A | N/A | N/A |
| −2 | 166/119 | N/A | N/A | N/A |
| −1 | 169/121 | N/A | N/A | N/A |
| 0 | 167/119 | N/A | N/A | N/A |
| 1 | 166/114 | 160/100 | 142/98 | 140/88 |
| 2 | 160/100 | 154/110 | 150/104 | 141/89 |
| 3 | 158/90 | 154/100 | 143/89 | 144/89 |
| 4 | 148/98 | 144/99 | 140/89 | 139/85 |
| 5 | 149/99 | 143/87 | 140/80 | 139/78 |
| 6 | 150/87 | 145/89 | 139/85 | 138/77 |
| 7 | 146/86 | 144/89 | 135/78 | 136/79 |
| 8 | 139/78 | 136/87 | 135/78 | 139/81 |
| 9 | 135/85 | 136/76 | 133/79 | 139/78 |
| 10 | 138/87 | 133/77 | 134/77 | 133/78 |
| 11 | 137/76 | 139/88 | 138/79 | 141/87 |
| 12 | 137/88 | 137/89 | 134/80 | 135/77 |
| 13 | 136/77 | 136/78 | 133/76 | 134/75 |
| 14 | 137/79 | 134/81 | 133/75 | 133/75 |
| 15 | 138/77 | 133/76 | 132/78 | 135/74 |
| 16 | 133/74 | 133/77 | 134/77 | 132/68 |
| 17 | 140/78 | 139/76 | 133/76 | 133/77 |
| 18 | 133/76 | 8/78 | 32/75 | 133/78 |
| 19 | 135/75 | 131/73 | 131/75 | 133/74 |
| 20 | 133/76 | 131/74 | 133/73 | 132/76 |
| 30 | 134/74 | 135/76 | 134/71 | 135/74 |
| 180 | 133/78 | 135/78 | 136/73 | 133/72 |

BP = Blood Pressure

Example 12

An eleven year old Labrador retriever had suffered from lick granulomas for at least 3 years. This condition of dogs are reportedly caused by nervousness wherein the dog continues to lick a certain site until an open wound is produced. Licking is continued and the open wound becomes significantly irritated and swollen. This dog's granuloma was located on the left hind leg above the pasturn. The swelling around the leg measured 8 inches in diameter and the open wound measured 4×3 inches. The dog had been treated with cortisone injections and hydrocortisone creams with little success. This dog was injected with 10 mg of sodium hyaluronate having a molecular weight ranging from 30,000 to 400,000 (1.0 mL intramuscularly—equivalent to 10 mg). The open wound began to heal. This injection was followed up with topical application of a low molecular weight hyaluronic acid prepared by making a 1% (wt/vol) solution of hyaluronic acid (Medex Ltd) containing 1% Wintergreen Oil (Loranne Oil), 1% Spearmint Oil (Loranne Oil) and 0.5% Peppermint Oil (Loranne Oil). The topical formulation was applied at least two times per day. Over a period of 2 months the lick granuloma healed completely and the swelling reduced to a diameter of 3 inches. The dog has not licked this area since treatment began. Therefore, the complex carbohydrates of the present invention are able to successfully treat lick granulomas (a previously untreatable condition of dogs) and eliminate the cause of the licking.

Example 13

Dogs often develop areas on their skin that become irritated and that they lick until the area is raw and oozing. Often these areas become infected with normal flora (bacteria) on the skin. Additionally, the hair around the area is usually either licked off or sloughs off. These areas are termed "hot spots". They are extremely difficult to treat and are thought to be caused by allergies to foods or environmental stimuli. Treatment generally includes cortisone by injection or by mouth followed by antibiotics (oral or topical) to treat the complication of bacterial infection. Three dogs with severe hot spots were treated with the complex carbohydrates of the present invention. Dog #1 had a large hot spot on the top of the head (diameter 3×2 inches) and smaller ones around the muzzle area. Dog #2 had a large hot spot on its back just in front of the tail.

This area measured approximately 6 inches in diameter. Dog #3 had hot spots down the back of both hind legs and on the groin area of both hind legs. Parenteral sodium hyaluronate was administered to Dog #1. This dog received 3×10 mg doses at one week intervals. The hot spot on dog #2 was treated with topical sodium hyaluronate. The formulation was the same as that described in EXAMPLE 15. The topical formulation was applied BID directly on the hot spot. Dog #3 received sodium hyaluronate administered orally. This dog received 5 mg BID on its food.

Hot Spots: Reports on the treatment progress were made by the owners and are shown in Table 2. Table 2 indicates that all of the treatments were effective. It appears that the parenterally administered sodium hyaluronate was slightly more effective than the orally or topically administered product. However, all were more effective than the previous treatments used. Additionally, none of the dogs have had recurrent hot spots, even one year after the initial treatment.

TABLE 2

Response of Dogs with Hot Spots to Treatment with Sodium Hyaluronate

| Days Post Treatment Initiation | Dog #1 | Dog #2 | Dog #3 |
|---|---|---|---|
| 1 | NC | NC | NC |
| 2 | Dog Quit Licking | NC | Dog Quit Licking |
| 3 | Drying | Dog Quit Licking | Drying |
| 4 | Same | Same | Same |
| 5 | Healing Well | Drying | Healing Well |
| 6 | Same | Same | Same |
| 7 | Same | Same | Same |
| 8 | Significantly improved | Healing Well | Significantly Improved |
| 9 | Same | Same | Same |
| 10 | Same | Significantly Improved | Same |
| 11 | Size now 1 inch in diameter | Same | Same |
| 12 | Same | Size now 2 inches in diameter | Size now 1 inch in diameter |
| 13 | Essentially healed | Same | Same |
| 14 | Same | Size now 1 inch in diameter | Essentially healed |
| 15 | Hair growing back | Essentially healed | Hair growing back |
| 16 | Hair growing back | Hair growing back | Hair growing back |
| 17 | Same | Same | Same |
| 18 | Same | Same | Same |
| 19 | Same | Same | Same |
| 20 | Completely healed | Can still see a slight lesion | Hair almost grown back |
| 21 | No new lesions | Same | Same |
| 22 | Same | Completely healed | Completely healed |
| 23 | Same | Same | Same |
| 24 | Same | Same | Same |
| 25 | Same | Same | Same |
| 26 | Same | Same | Same |
| 27 | Same | Same | Same |
| 28 | Same | Same | Same |
| 29 | Same | Same | Same |

NC = No Change

Example 14

An 83 year old female suffered from chronic eczema—scaly and red areas on her neck and arms. She had also been diagnosed with a yeast infection associated with the eczema. She had tried all types of treatments, including cortisone with no significant effect. She initially used a topical preparation prepared according to this invention. This contained a mixture of low and high molecular weight sodium hyaluronate (prepared as in EXAMPLE 1) mixed with 1% Wintergreen Oil, 1% Spearmint Oil, and 0.5% Peppermint Oil. She applied it topically for four weeks. She noted that the bright redness of the eczema subsided. However, there was still itching and redness. She then began to orally take the 1% mixture, of low and high molecular weight sodium hyaluronate described in example 1. She reported that within 2 weeks all signs of the eczema had disappeared, the itching was gone and she felt better than she had felt for years. The oral dose required was 5 mg TID for this 91 pound female. Therefore, the dose was 0.05 mg/Kg. This demonstrates that the complex carbohydrates of the present invention is effective in treating severe cases of eczema even when they are complicated with a yeast infection.

Example 15

In order to determine whether low doses of other complex carbohydrates taken orally or mucosally could show effects similar to hyaluronic acid, 3 patients presenting with Lupus Erythematosis, interstitial cystitis and high blood pressure were treated with oral liquid chondroitin sulfate. None of these patients had taken chondroitin sulfate previously. A 5% (wt/vol) solution of chondroitin sulfate (Infinity Laboratories, Inc) without essential oils was prepared. This was dispensed into 30 ml bottles and provided to the three patients with instructions to take 1.0 mL orally BID, holding it in the mouth for approximately 10 seconds prior to swallowing it. This represented a dose of 5 mg BID. The weight of the two patients were 155 lbs and 128 lbs, respectively. Therefore, the doses administered were 0.07 mg/Kg and 0.09 mg/Kg. This provided relief (within 15 minutes). However, the relief lasted only 1-3 hours. The patients reported that they had to take the chondroitin Sulfate solution three to five times per day to obtain successful treatment. After two months of this regimen, the patients were given a mixture of the 5% chondroitin sulfate and 1% high molecular weight hyaluronic acid. They were instructed to take this as often as necessary. Each reported that this product was effective when taken only 2 times per day and the effect lasted from 8 to 10 hours for the Lupus patient and for the interstitial cystitis patient. This demonstrates that a mixture of low and high molecular weight complex carbohydrates is more effective and that significantly lower doses (100 to 1000 fold less than currently suggested for OTC use) of chondroitin sulfate are required for more effective treatment of Lupus Erythematosis, interstitial cystitis and high blood pressure. Chondroitin sulfate is widely known and used in tablets for arthritis. However, it is used for such treatment at very high doses (greater than 1000 mg per day). We have found that very low concentrations when administered in liquid form orally, mucosally or topically, is more effective than the higher doses in a powder form. Additionally, the inventors are not aware of any use of chondroitin sulfate for any of our other indications of the treatments and diseases listed.

Example 16

A 55 year old female and a 56 year old male felt that they were coming down with a cold. Both had oral sodium hyaluronate prepared as described in EXAMPLE 1 available to them and began taking a 3 to 5 mg dose orally every 3 to 4 hours. They commented that the pain of the sore throat was gone within 15 minutes of taking the oral preparation. Additionally, the cold seemed to be very mild and quickly progressed through the normal stages, each stage being much milder than normal for these individuals. The female reported that her cold lasted only 4 days as compared with her historical colds that lasted 21 to 24 days. The male reported that he seldom noticed the symptoms of his cold and felt fine in 3 to 4 days. Historically, his colds lasted approximately 14 days. These results indicate that the complex carbohydrates of the present invention reduce the symptoms of colds and that they have anti-viral activity.

Example 17

In order to determine whether scar tissue could be reduced by application of the complex carbohydrates of the present invention. Sodium hyaluronate having a molecular weight range of between 10,000 and 2 million was formulated so that it could be used as a scar reduction patch. The formulation was prepared as follows: To 50 mL of 1% sodium hyaluronate (Medex Ltd) was added 7 grams of alphy-hydroxy acid. The solution was mixed until a clear solution was produced. Then 20 mL of USP Glycerol was added and this was mixed to homogeniety. Finally, 1% sodium hyaluronate was added to QS the volume to a total of 100 mL. After the final HA addition, the solution thickened and was spread evenly on the bottom of a petri dish. It was allowed to dry for 48 hours at room temperature after which it was used to treat a fresh scar produced as a result of reconstructive surgery on the left hand of a 50 year old female patient. The solidified HA was cut into a shape slightly larger than the scar. It was applied over the scar and held in place by applying an ace bandage. Approximately ½ of the scar was left untreated so as to serve as a control. The Bandage was allowed to remain over the scar for a period of 2 weeks. Intermittently, the HA patch was removed and the scar was cleaned. If the solidified HA patch dried out, it was moistened slightly with water and reapplied. After only two weeks of application the raised scar tissue (adhesion) had essentially disappeared. This demonstrates that scar reduction can be accomplished by use of the complex carbohydrates of the present invention.

Example 18

In order to determine whether open wounds could be stimulated to heal faster, gauze was soaked in 1% sodium hyaluronate having a molecular weight range from 30,000 to 500,000 and allowed to dry. This HA-containing gauze was applied to open wounds of the following types: 1) a rug burn produced by sliding on artificial turf on a football field; 2) a surgical wound resulting from a hip replacement; and 3) a cut finger resulting from a piece of broken glass. The bandages were kept on the wounds until they were healed well enough to remain uncovered. It was reported that the rug burn was healed within 3 days. This compared with a 2 week healing period normally experienced by this patient. The surgical wound healed within 5 days, again almost 10 days sooner than expected. The cut finger was healed within 3 days. The conclusion was that a glycosaminoglycan is very effective in stimulating wound healing when incorporated into gauze and used as a bandage.

Example 19

Ten patients taking oral preparations of 1% sodium hyaluronate (1 taking low molecular weight ranging (from 10,000 to 300,000), 4 taking medium molecular weight (ranging from 100,000 to 600,000), and 5 taking high molecular weight (ranging from 500,000 to 2 million), reported separately that they had noticed the following positive effects in addition to the treatment effects for which they were taking the complex carbohydrate. They were impressed in the increased cognitive effects that they noticed. They reported that their memory had significantly improved as had their ability to focus on information and tasks (cognitive function). Additionally, each reported that they experienced thickening of their hair and fingernails as well as improvement in their skin condition (their skin was more supple and the wrinkles in their face were reduced). These effects resulted directly from the use of the complex carbohydrates of the present invention.

Example 20

Four of the patients taking oral or mucosal complex carbohydrates (1 taking 5% chondroitin sulfate and three taking 1% sodium hyaluronate with a molecular weight range from 30,000 to 500,000) have reported that, prior to taking the complex carbohydrates of the present invention, they had been plagued with repeated vaginal yeast infections. All had been suffering from yeast infections at the initiation of the present treatment. They were not taking other medications to treat these yeast infections. All four patients reported that their yeast infections disappeared within 3 to 7 days of beginning treatment with the complex carbohydrates of the present invention. They have remained on the present treatments for approximately 14 months and have remained yeast infection free. It is concluded that the complex carbohydrates of the present invention are able to treat and/or prevent yeast infections.

All cited patents, provisional applications, publications and PCT applications referred to in this application are herein incorporated by reference.

Although the invention has been described in detail in the foregoing, for the purpose of illustration it is to be understood that such detail is solely for that purpose and that variations can be made therein by those skilled in the art without departing from the spirit and scope of the invention except as it may be limited by the claims.

What is claimed is:

1. A method of treating autism comprising administering hyaluronic acid or a salt thereof as an active ingredient to a patient in need thereof.

2. The method according to claim 1, wherein the hyaluronic acid or salt thereof is administered orally, mucosally or parenterally.

3. The method according to claim 1, wherein the hyaluronic acid or salt thereof comprises at least on fraction having a molecular weight of at least 1,000,000 daltons.

* * * * *